(12) United States Patent
Wurster (10) Patent No.: US 10,512,794 B2
(45) Date of Patent: Dec. 24, 2019

(54) STEREOTACTIC FRAME

(71) Applicant: BRAINSONIX CORPORATION, Sherman Oaks, CA (US)

(72) Inventor: Walter William Wurster, Reno, NV (US)

(73) Assignee: BRAINSONIX CORPORATION, Sherman Oaks, CA (US)

( * ) Notice: Subject to any disclaimer, the term of this patent is extended or adjusted under 35 U.S.C. 154(b) by 327 days.

(21) Appl. No.: 15/382,351

(22) Filed: Dec. 16, 2016

(65) Prior Publication Data
US 2018/0169443 A1   Jun. 21, 2018

(51) Int. Cl.
*A61N 7/00* (2006.01)
*A61B 90/10* (2016.01)
*A61B 90/00* (2016.01)

(52) U.S. Cl.
CPC .............. *A61N 7/00* (2013.01); *A61B 90/10* (2016.02); *A61B 2090/374* (2016.02); *A61N 2007/0026* (2013.01); *A61N 2007/0091* (2013.01)

(58) Field of Classification Search
CPC ...................... A61N 7/00–02; A61B 90/10–18
See application file for complete search history.

(56) References Cited

U.S. PATENT DOCUMENTS

| | | |
|---|---|---|
| 4,343,301 A | 8/1982 | Indech |
| 5,247,935 A | 9/1993 | Cline et al. |
| 5,275,165 A | 1/1994 | Ettinger |
| 5,291,890 A | 3/1994 | Cline |
| 5,323,779 A | 6/1994 | Hardy |
| 5,381,794 A | 1/1995 | Tei et al. |
| 5,409,446 A | 4/1995 | Rattner |
| 5,546,438 A | 8/1996 | Hynecek |
| 5,738,625 A | 4/1998 | Gluck |
| 5,752,515 A | 5/1998 | Jolesz |
| 6,066,123 A | 5/2000 | Li |
| 6,088,613 A | 7/2000 | Unger |
| 6,094,598 A | 7/2000 | Elsberry |

(Continued)

OTHER PUBLICATIONS

Yoo, et al., Focused ultrasound modulates region-specific brain activity, Elsevier Journal—NeuroImage, vol. 56, 2011, pp. 1267-1275.

(Continued)

*Primary Examiner* — Eric D. Bertram
(74) *Attorney, Agent, or Firm* — Schwabe Williamson & Wyatt, PC (57) ABSTRACT

A stereotactic frame includes a vertical column that extends up from a base. A first laterally extending support arm extends from a first side of the column and a second laterally extending support arm extends from a second side of the column. One of the first or second support arms may include a transducer assembly. The transducer assembly may move a focal point of the transducer in different lateral and longitudinal horizontal positions and different vertical positions. The transducer assembly also may move the focal point of the transducer beam into different pivoting angled positions. The stereotactic frame applies repeatable ultrasonic energy to targets inside a patient without using invasive attachment procedures and without having to repeatedly use expensive magnetic resonance imaging (MRI) machines.

13 Claims, 9 Drawing Sheets

(56) References Cited

U.S. PATENT DOCUMENTS

| | | | |
|---|---|---|---|
| 6,148,225 | A | 11/2000 | Kestler et al. |
| 6,198,956 | B1 | 3/2001 | Dunne |
| 6,198,958 | B1 | 3/2001 | Ives |
| 6,261,231 | B1 | 7/2001 | Damphousse et al. |
| 6,267,734 | B1 | 7/2001 | Ishibashi |
| 6,348,793 | B1 | 2/2002 | Balloni |
| 6,413,216 | B1 | 7/2002 | Cain et al. |
| 6,612,988 | B2 | 9/2003 | Maor |
| 6,708,051 | B1 | 3/2004 | Durousseau |
| 7,283,861 | B2 | 10/2007 | Bystritsky |
| 7,300,414 | B1 | 11/2007 | Holland |
| 7,427,265 | B1 | 9/2008 | Keilman |
| 7,450,985 | B2 * | 11/2008 | Meloy ............... A61B 5/0555 128/870 |
| 7,505,807 | B1 | 3/2009 | Kucharczyk |
| 8,086,296 | B2 | 12/2011 | Bystritsky |
| 8,343,083 | B1 | 1/2013 | Fencel |
| 9,061,133 | B2 | 6/2015 | Wurster |
| 9,630,029 | B2 | 4/2017 | Wurster |
| 2002/0042121 | A1 | 4/2002 | Riesner |
| 2002/0127230 | A1 | 9/2002 | Chen |
| 2002/0173697 | A1 | 11/2002 | Lenhardt |
| 2003/0204135 | A1 | 10/2003 | Bystritsky |
| 2004/0048795 | A1 | 3/2004 | Ivanova |
| 2005/0020945 | A1 | 1/2005 | Tosaya |
| 2005/0240126 | A1 | 10/2005 | Roley |
| 2006/0184069 | A1 | 8/2006 | Vaitekunas |
| 2007/0016031 | A1 | 1/2007 | Mourad et al. |
| 2007/0299370 | A1 | 12/2007 | Bystritsky |
| 2008/0262350 | A1 | 10/2008 | Unger |
| 2008/0275340 | A1 | 11/2008 | Beach |
| 2009/0005711 | A1 | 1/2009 | Konofagou |
| 2009/0112133 | A1 | 4/2009 | Deisseroth |
| 2010/0010394 | A1 | 1/2010 | Liu |
| 2011/0092800 | A1 | 4/2011 | Yoo |
| 2011/0094288 | A1 | 4/2011 | Medan |
| 2011/0172653 | A1 | 7/2011 | Schneider |
| 2011/0213200 | A1 | 9/2011 | Mishelevich |
| 2012/0060847 | A1 * | 3/2012 | Stratton ............... A61B 19/203 128/845 |
| 2012/0083719 | A1 | 4/2012 | Mishelevich |
| 2014/0058293 | A1 | 2/2014 | Hynynen et al. |
| 2014/0186423 | A1 | 7/2014 | Gelfand |
| 2014/0188011 | A1 * | 7/2014 | Wurster ............... A61N 7/02 601/2 |
| 2016/0067526 | A1 | 3/2016 | Yang |
| 2017/0182339 | A1 | 6/2017 | Wurster |

OTHER PUBLICATIONS

Mulgaonkar et al., A prototype stimulator system for noninvasive low intensity focused ultrasound delivery; Stud Health Technol Inform, vol. 173, 2012, pp. 297-303.

Min et al, Focused ultrasound-mediated suppression of chemically-induced acute epileptic EEG activity, BMC Neuroscience; 2011, 12:23, pp. 1-12.

Bystritsky et al., A review of low-intensity focused ultrasound pulsation, Elsevier Journal—Brain Stimulation, vol. 4, 2011, pp. 125-136.

Barlow, et al., The risk of seizure after receipt of whole-cell pertussis or measles, mumps, and rubella vaccine, New England journal of Medicine, vol. 345, No. 9, pp. 656-661 (2001).

Tyler, et al., Remote excitation of neuronal circuits using low-intensity, low-frequency ultrasound, PlosOne, vol. 3, Issue 10, pp. 1-11 (Oct. 2008).

Turfail, et al., Ultrasonic neuromodulation by brain stimulation with transcranial ultrasound, Nature Protocols, vol. 6, No. 9, pp. 1453-1470 (2011).

Clement et al., A hemisphere array for non-invasive brain therapy and surgery, Physics in Medicine and Biology, vol. 45, No. 12, pp. 3707-3719 (2000).

Colucci et al., Focused ultrasound effects on nerve action potential in vitro, Ultrasound in Med. & Biol., vol. 35, No. 10, pp. 1737-1747 (2009).

Tufail, et al., Transcranial Pulsed Ultrasound Stimulates Intact Brain Circuits, Neuron, vol. 66, pp. 681-694 (Jun. 10, 2010).

Yang, et al., Transcranial focused ultrasound to the thalamus is associated with reduced extracellular GABA levels in rats, Neruopsychobiology, vol. 65, pp. 153-160 (2012).

Yoo, et al., Transcranial focused ultrasound to the thalamus alters anesthesia time in rats, Neuroreport, vol. 22(15), pp. 783-787 (Oct. 26, 2011).

Hameroff, et al., Transcranial ultrasound (TUS) effects on mental states: a pilot study, Brain Stimulation, vol. 6, pp. 409-415 (2013).

Korb, et al., Low-intensity focused ultrasound pulstation device used druing magnetic resonance imaging: evaluation of magnetic resonance imagin-related heating at 3 tesla/128MHz, Neuromodulation, (2013).

Bystritsky et al., A preliminary study of fMRI-guided rTMS in the treatment of generalized anxiety disorder, J Clin Psychiatry, vol. 69, pp. 1092-1098 (Jul. 7, 2008).

Deffieux et al., Low-intensity focused ultrasound modulates monkey visuomotor behaviour, Current Biology, vol. 23, pp. 2430-2433 (Dec. 2, 2013).

Mehic et al., Increased anatomical specificity of neuromodulation via modulated focused ultrasound, Plos One, vol. 9, Issue 2, pp. 1-13 (Feb. 2014).

Kim et al., Estimation of the spatial profile of neuromodulaton na dthe temporal latency in motor responses induced by focused ultrasound brain stimulation, Neurophysiology Neuroreport, vol. 25, No. 7., pp. 475-479 (2014).

Metwally, et al., Influence of the anitsotropic mechanical properties of the skull in low-intensity focused ultrsound towards neuromodulation of the brain, 35th Ann Int Conf of IEEE EMBS, Osaka, Japan pp. 4565-4568 (Jul. 3-7, 2013).

Winhye, et al., Creation on various skiin sensations using pulsed focused ultrasound: evidence for functional neuromodulation, International Journal of Imaging Ssytems and Technology, (Dec. 27, 2013).

Tyler et al., Remote excitation of neuronal circuits using low intensity , low frequency ultrasound, Ultrasonic Neurostimulation, vol. 3, No. 10, pp. 1-11 (2008).

Tyler, W.J., Noninvasive Neuromodulation with Ultrasound? A continuum mechanics hypothesis, pp. 1-12 (2010).

Jordao, JF et al., "Amyloid-beta plaque reduction, endogenous antibody delivery and glial activation by brain-targeted, transcranial focused ultrasound," Exp Neurol. Oct. 2013; 248: 16-29. Published online May 21, 2013; retrieved from the Internet <https://www.sciencedirect.com/science/article/pll/S0014488613001544?via%3Dihub> <doi: 10.1016/j.expneurol.2013.5.008>.

Leinenga, G., et al. "Scanning ultrasound removed amyloid-beta and restores memory in an Alzheimer's disease mouse model," Scie Transl Med.; Mar. 11, 2015; 7 (278):278ra33. Retrieved from the Internet <http://stm.sciencemag.org/content/7/278/278ra33> <doi:10.1126/scitranslmed.aaa2512>.

* cited by examiner

STEREOTACTIC FRAME

BACKGROUND

Ultrasonic energy is used to treat different medical conditions. During treatment, transducers apply ultrasonic energy to a treatment zone or "target" within a patient. For example, the ultrasonic energy may be applied to a clot to dissolve or remove a blockage within the brain. Of course other types of disorders also may be treated with ultrasonic energy. For example, ultrasonic therapy may be used for treating other psychiatric, neurological, and medical disorders.

Ultrasonic therapy may involve applying ultrasonic energy to the same treatment zone over multiple treatment sessions. Each treatment session needs to apply the ultrasonic energy accurately and repeatedly to the same treatment zone. A Magnetic Resonance Imaging (MRI) machine may first scan the brain, or other body part, to locate the target area. The ultrasonic system is then adjusted to focus the ultrasonic energy onto the located target area. Ultrasonic therapy may be time consuming and expensive since each session requires a trip to a hospital and use of a MRI machine to relocate the same target area. Ultrasonic therapy is also invasive since holes are often drilled into the head of a patient to secure the existing stereotactic frame designs.

DETAILED DESCRIPTION

A stereotactic frame includes a vertical column that extends up from a base. A first laterally extending support arm extends from a first side of the column and a second laterally extending support arm extends from a second side of the column. One of the first or second support arms may include a transducer assembly. The transducer assembly may move a focal point of the transducer in different lateral and longitudinal horizontal positions and different vertical positions. The transducer assembly also may move the focal point of the transducer beam into different pivoting angled positions. The stereotactic frame applies repeatable ultrasonic energy to targets inside a patient without using invasive attachment procedures and without having to repeatedly use expensive magnetic resonance imaging (MRI) machines. A base support may attach to the stereotactic frame for subsequent treatments without using a MRI machine.

In one example, the stereotactic frame is particularly well suited for treating degenerative dementia such as Alzheimer's disease and memory loss. The stereotactic frame may retain a low intensity focused ultrasound pulsation (LIFUP) device (ultrasound device) used for removing substances that accumulate in the interstitial spaces that are believed to be at least partially responsible for degeneration seen in Alzheimer's disease and other degenerative processes. The stereotactic frame provides repeatable lateral, longitudinal, and pivoting positioning of the ultrasound device so emitted ultrasonic waves can be repeated focused at the same target areas, such as the hippocampus and parahippocampal gyrus, that may be associated with degenerative dementia.

Figure 1A:
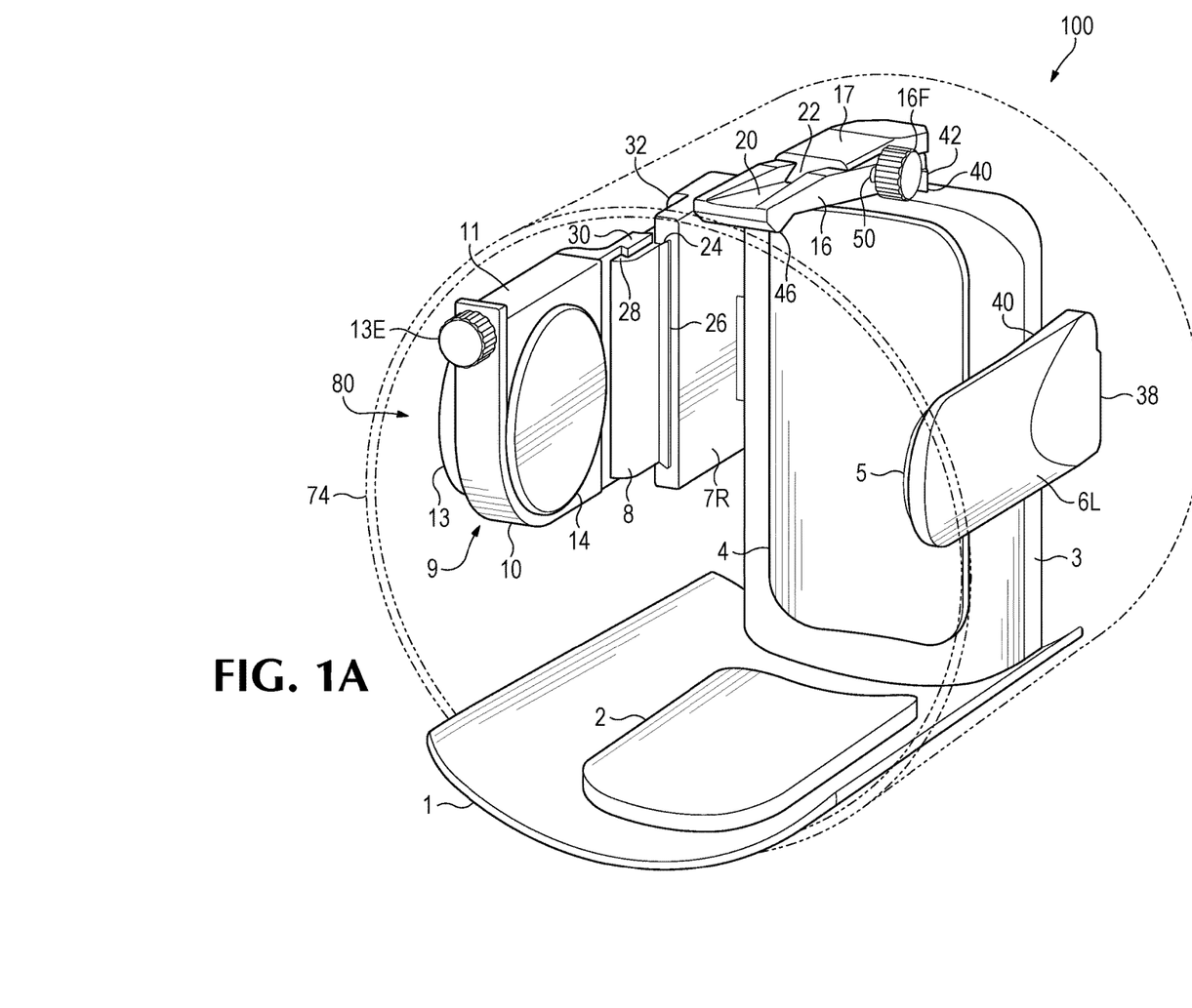
FIG. 1A shows a perspective view of a stereotactic frame.
Figure 1B:
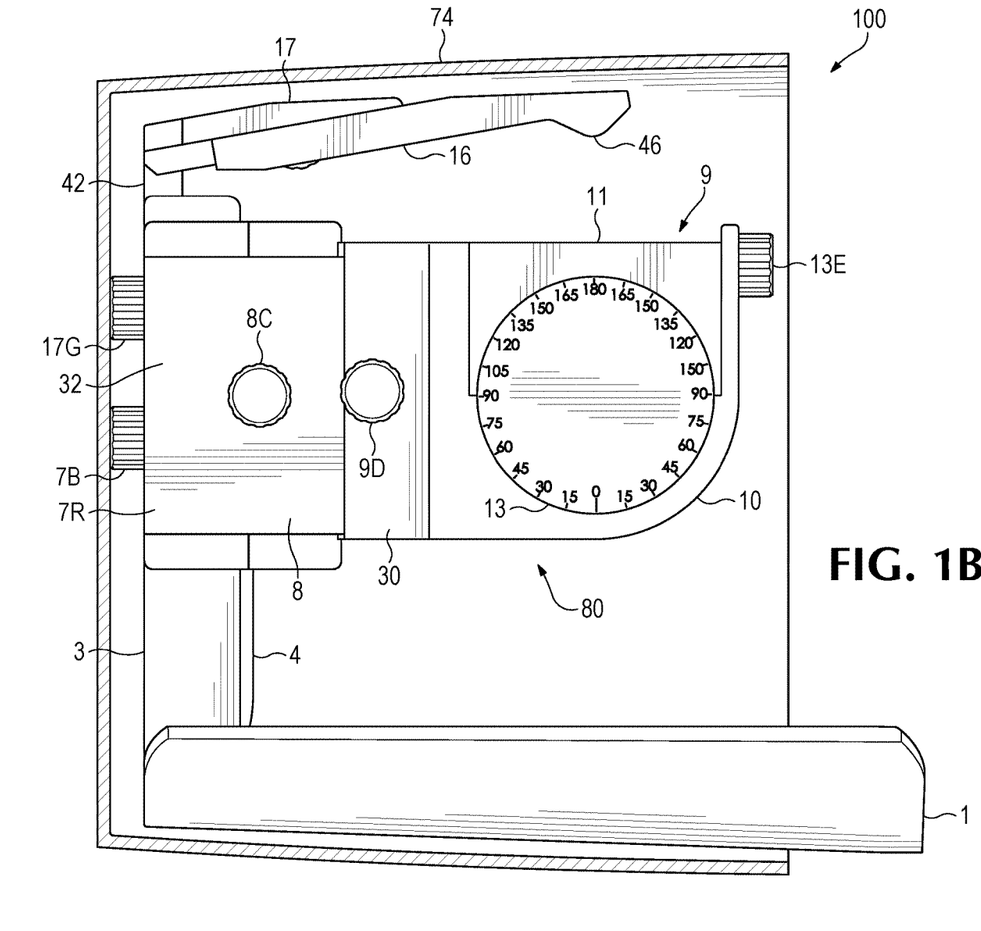
FIG. 1B shows a tight side view of the stereotactic frame.
Figure 1C:
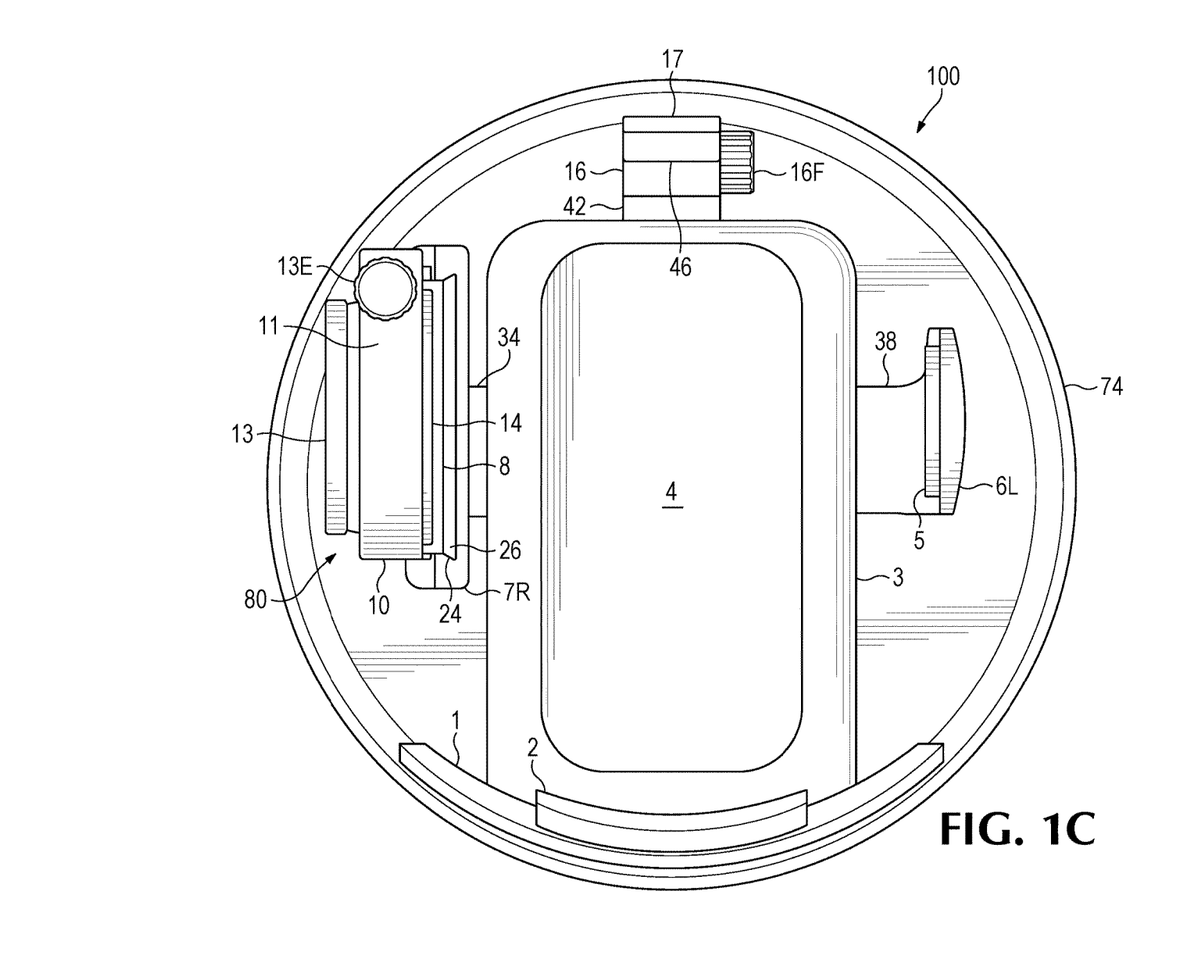
FIG. 1C shows a front view of the stereotactic frame.
Figure 1D:
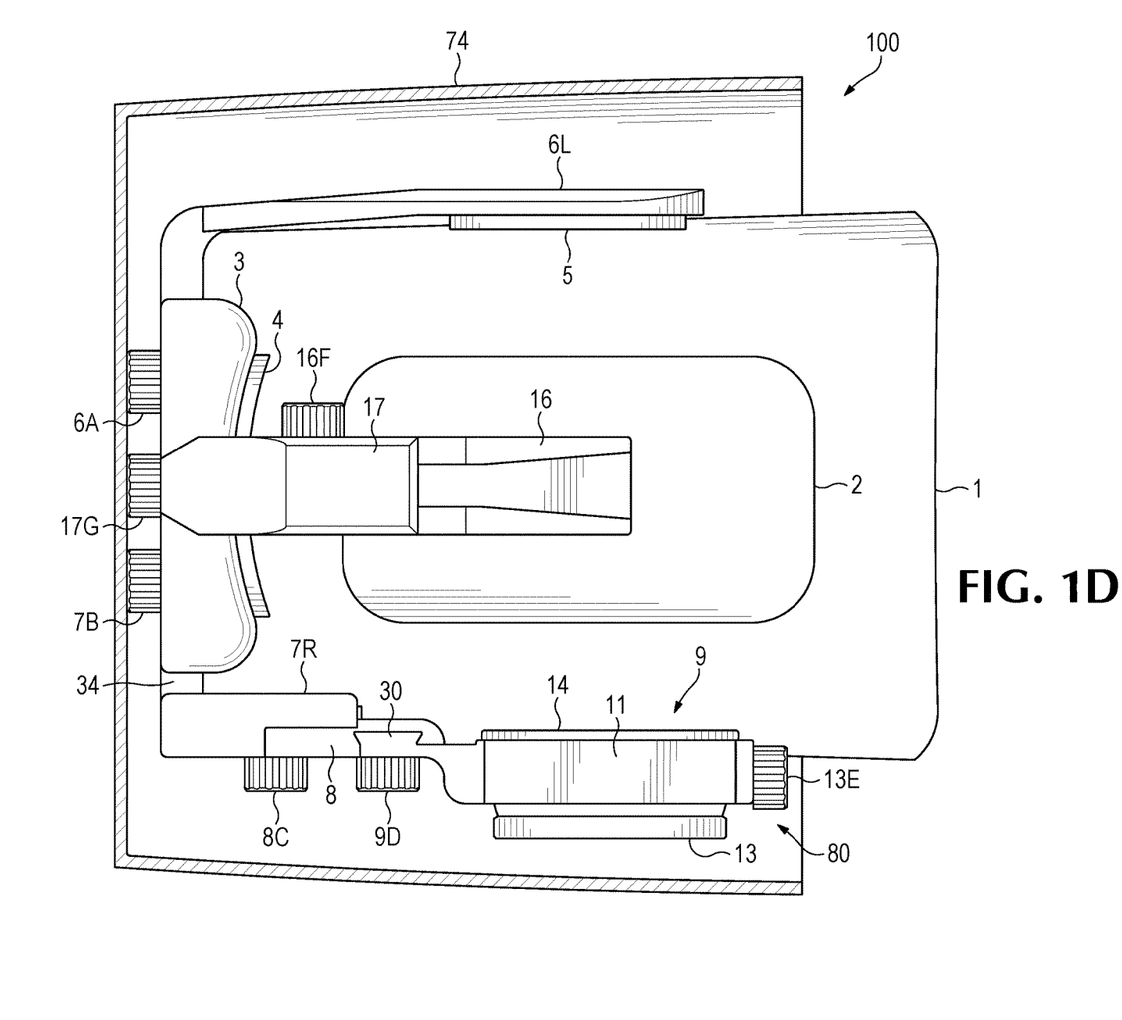
FIG. 1D shows a top view of the stereotactic frame.

FIG. 1A shows a front perspective view of a stereotactic frame 100, FIG. 1B shows a right side view of stereotactic frame 100, FIG. 1C shows a front view of frame 100, and FIG. 1D shows a top view of frame 100. Frame 100 may locate a patients head and may apply ultrasonic energy to precise target locations within the patient.

The explanation below discusses the specific example of using frame 100 to apply ultrasonic energy to a target location within the head of the patient. However, it should be understood that head frame 100 may apply any type of sonic, magnetic, or any other alternative energy to any target location within any body part of the patient. Frame 100 may be used on human patients or animal patients. In another example, frame 100 may provide head stabilization without necessarily applying ultrasonic energy to the patient.

Referring to FIGS. 1A, 1B, 1C, and 1D, a vertical column 3 extends up from a base member 1. A left side arm 6L slidingly attaches to a left side of vertical column 3 and a right side arm 7R slidingly attaches to a right side of vertical column 3. A nasal root arm 17 slidingly attaches to a top side of vertical column 3.

A removable horizontal cushion 2 extends over a top surface of base member 1, a vertical cushion 4 extends over a front face of vertical column 3, and a side cushion 5 extends over an inside face of left side arm 6L. In one example, cushions 2, 4, and 5 may have an adhesive, double sided tape, snaps, Velcro® hook and eye, or other securing material on a back side for attaching and detaching to base 1, vertical column 3, and left side arm 6L, respectively. Cushions 2, 4, and 5 may be formed from cloth, plastic, foam, or any other material.

Left side arm 6L, may include a right angled extension member 38 with angled dovetailed top and bottom sides that slidingly insert into a dovetailed slot 40 extending into the left side of vertical column 3. A knob 6A screws into a threaded hole formed in member 38 and holds left side arm 6L in selectable lateral positions out from the left side of vertical column 3.

Nasal root arm 17 may include a vertical downwardly extending member 42 with oppositely angled dovetailed sides that slidingly insert into a dovetailed slot 40 extending vertically down into the top side of vertical column 3. A knob 17G screws into a threaded hole formed in member 42 to hold root arm 17 into selectable vertical positions above a top end of vertical column 3.

An adjustment member 16 includes a protuberance 46 on a front end to place into a nasal root of a patient. A dovetailed rail 22 is formed on a bottom side of nasal root arm 17 and slides at a slight angle into an elongated dovetailed slot 20 formed in an upper side of adjustment member 16. Adjustment member 16 may include a slot or threaded hole for receiving a knob 16F that locks adjustment member 16 against nasal root arm 17 into different angled horizontal longitudinal positions in front of vertical column 3.

A transducer assembly 80 may include a side arm 7R, an adjustment member 8, and a transducer cradle 9. Side arm 7R may include a right angled extension member 34 with angled top and bottom dovetailed sides that slidingly insert into a slot 36 (shown below) with oppositely inclining top and bottom dovetailed sides extending into the right side of vertical column 3. A knob 7B pulls against the dovetail slot 34 holding side arm 7R in selectable horizontal lateral positions out from the right side of vertical column 3.

Transducer adjustment member 8 may include a dovetailed rail 26 that slides horizontally in and out of a dovetailed socket 24 that extends horizontally rearward into side arm 7R Side arm 7R includes a channel opening 32 that adjustment member 8 slides horizontally through to move forward and back along the right side of vertical column 3. Transducer cradle 9 may include a dovetailed rail 30 that slides vertically up and down in a dovetail socket 28 that extends vertically into an outside surface of adjustment member 8.

A knob 8C screws into and through a threaded hole and pushes against an opposite portion of side arm 7R selectively locking adjustment member 8 into different horizontal longitudinal positions. An adjustment knob 9D screws into a threaded hole formed in transducer cradle 9 and pushes against adjustment member 8 selectively locking cradle 9 into different vertical positions.

Transducer cradle 9 may include a lower U-shaped cradle section that forms a top opening for slidingly receiving and extending around a lower portion of a round transducer 13. An upper cradle section 11 may slide down into the U-shaped opening formed in the top of lower cradle section 10 and include an inverted U-shaped opening for extending over a top portion of transducer 13.

A transducer tightening knob 13E may insert into a threaded hole formed in a top end of lower cradle section 10 and pull against and hold upper cradle section 11 and transducer 13 in the U-shaped opening formed in lower cradle section 10.

Stereotactic frame 100 is shown located within a MRI head coil 74. In one example, head coil 74 have a round outside shape. A height and width of stereotactic frame 100 are sized to fit within head coil 74. The curved shape of base 1 is also sized to have a conforming radius with the inside surface of head coil 74.

Figure 2:
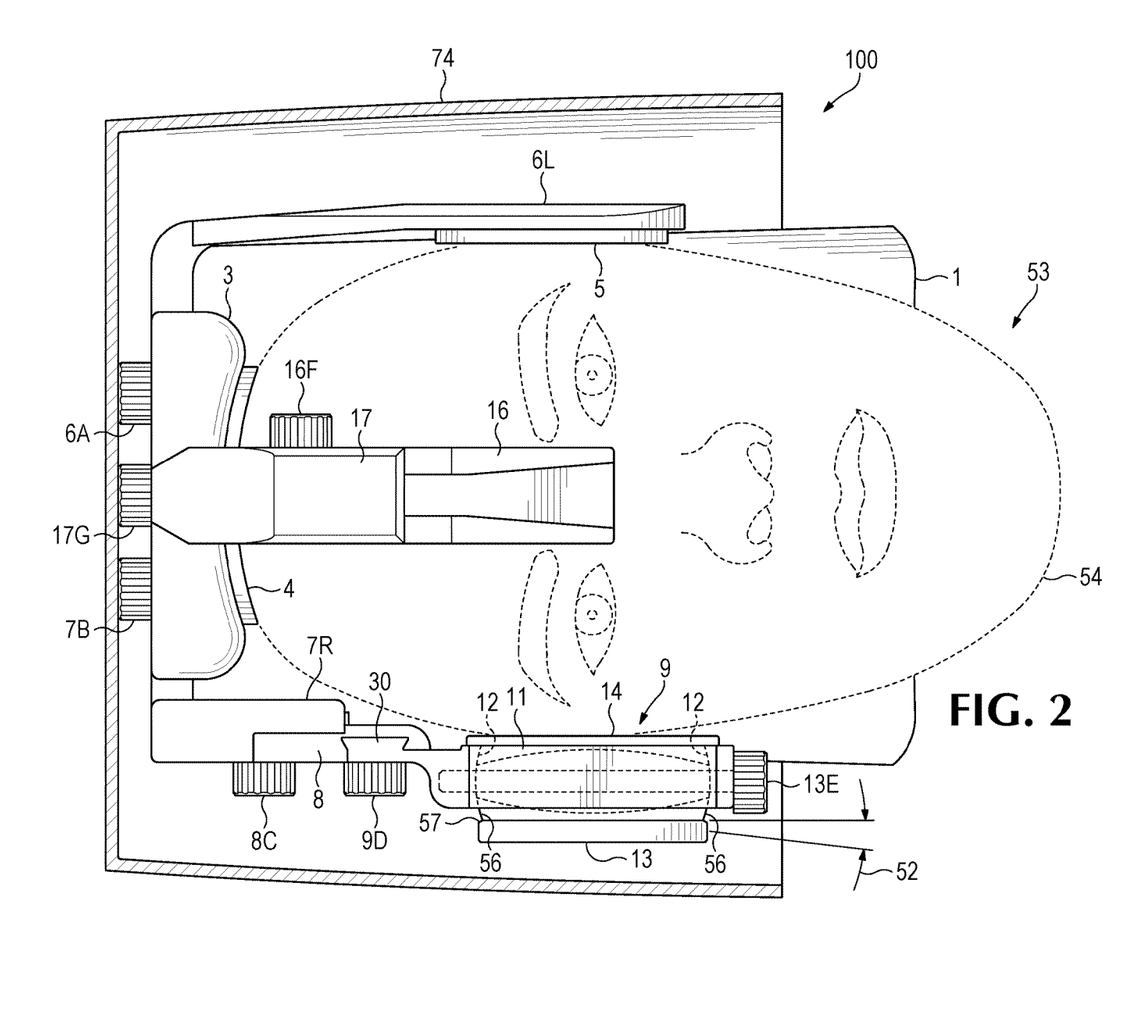
FIG. 2 is a top view of the stereotactic frame with a right transducer assembly.

FIG. 2 shows a top view of stereotactic head frame 100 holding head 54 of a patient 53. The opening formed in transducer cradle 9 includes rounded inside walls 12 for holding a rounded outside casing 56 of transducer 13. The rounded inside walls 12 of transducer cradle 9 and rounded outside walls 12 of casing 56 allow transducer 13 to pivot at different angles 52 inside of transducer cradle 9. In one example, pivot angle 52 can vary around 5 degrees. However, the pivot angle 52 can vary depending on the size and curvature of cradle 9 and transducer casing 56

An operator may loosen knob 13E and push the back of casing 56 to move transducer 13 into different pivot angles 52. Knob 13E is then tightened to hold transducer 13 in the selected pivot angle 52. Transducer cradle 9 may also include a stop 57 to limit the amount of pivoting for transducer 13.

A gel pack 14 may attach onto an inside face of transducer cradle 9 for pressing against a right side of head 54. Alternatively, gel pack 14 may attach to an inside surface of transducer casing 56.

Figure 3:
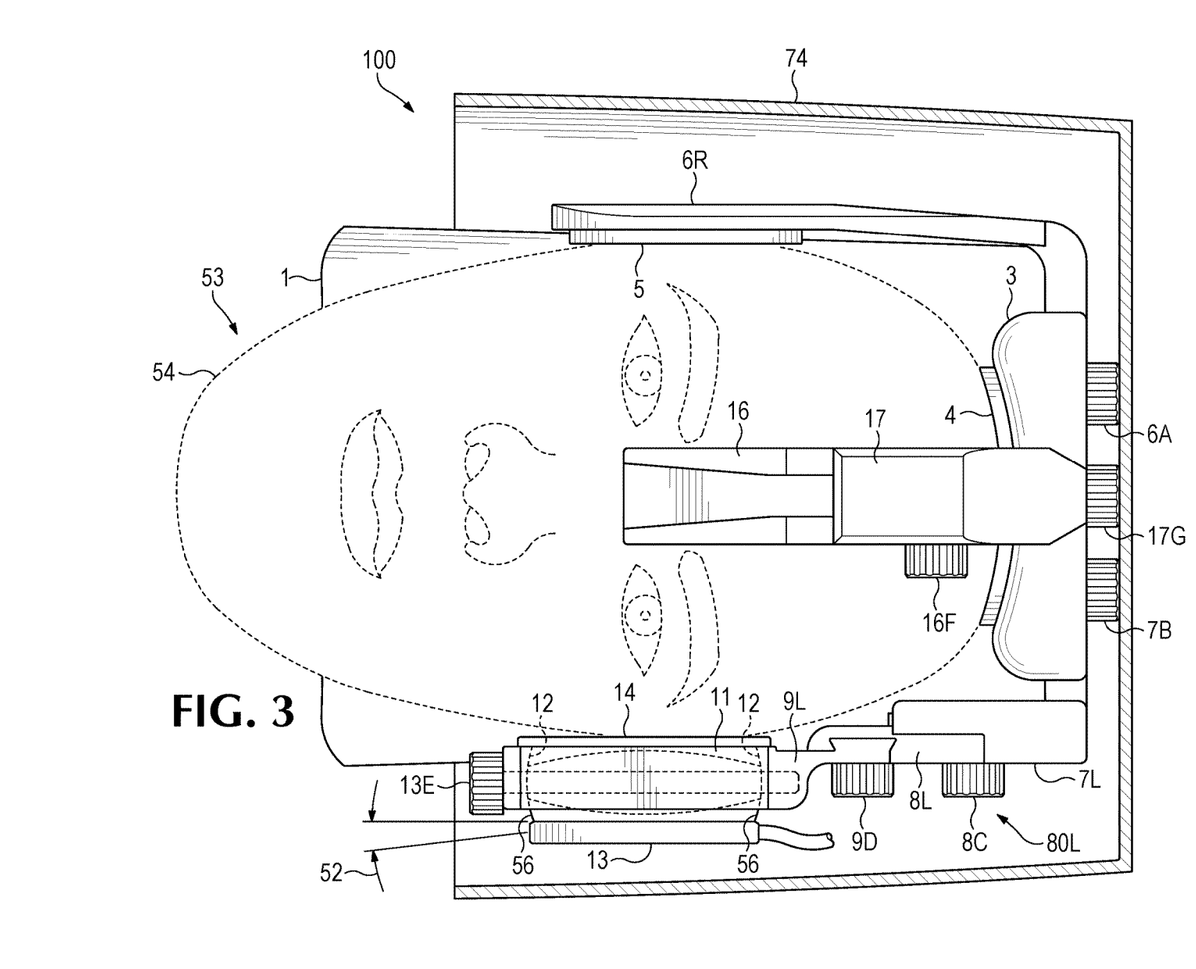
FIG. 3 is a top view of the stereotactic frame with a left transducer assembly.

FIG. 3 shows an alternative configuration of stereotactic frame 100 where a transducer assembly 80L attaches to the left side of column 3 and a support arm 6R attaches to the right side of column 3. Transducer assembly 80L includes the same elements as transducer assembly 80 described above but with a mirrored configuration. For example, a support arm 7L extends from the left side of column 3, adjustment member 8L slides horizontally and longitudinally in support arm 7L, and transducer cradle 9L slides vertically inside of adjustment member 8L. Support arm 6R also may operate the same as support arm 6L described above, but also may have a mirrored configuration.

In another example, stereotactic frame 100 may attach left support arm 6L in FIGS. 1A-1D to the left side of column 3 and attach right support arm 6R to the right side of column 3. Frame 100 may use this arrangement for applications where head 54 of patient 53 needs to be immobilized but does not need the application of ultrasound waves by transducer 13. For example, stereotactic frame 100 may use support arms 6L and 6R to immobilize head 54 of a victim at an accident scene while being transported to a hospital. Support 18 or some other support with a flat bottom may be attached to stereotactic frame 100 to prevent rocking.

Figure 4A:
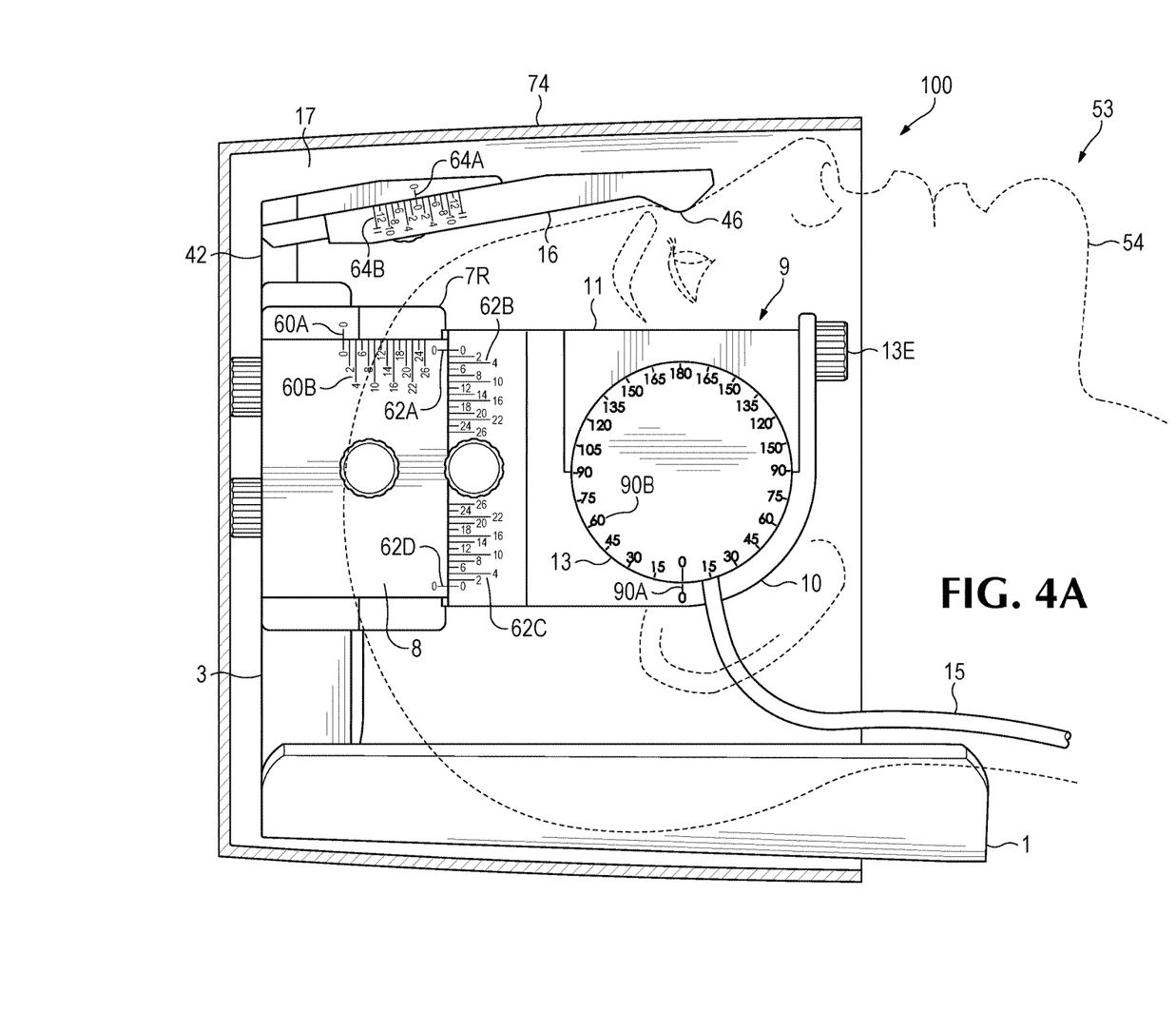
FIGS. 4A and 4B show reference markings on the stereotactic frame.
Figure 4B:
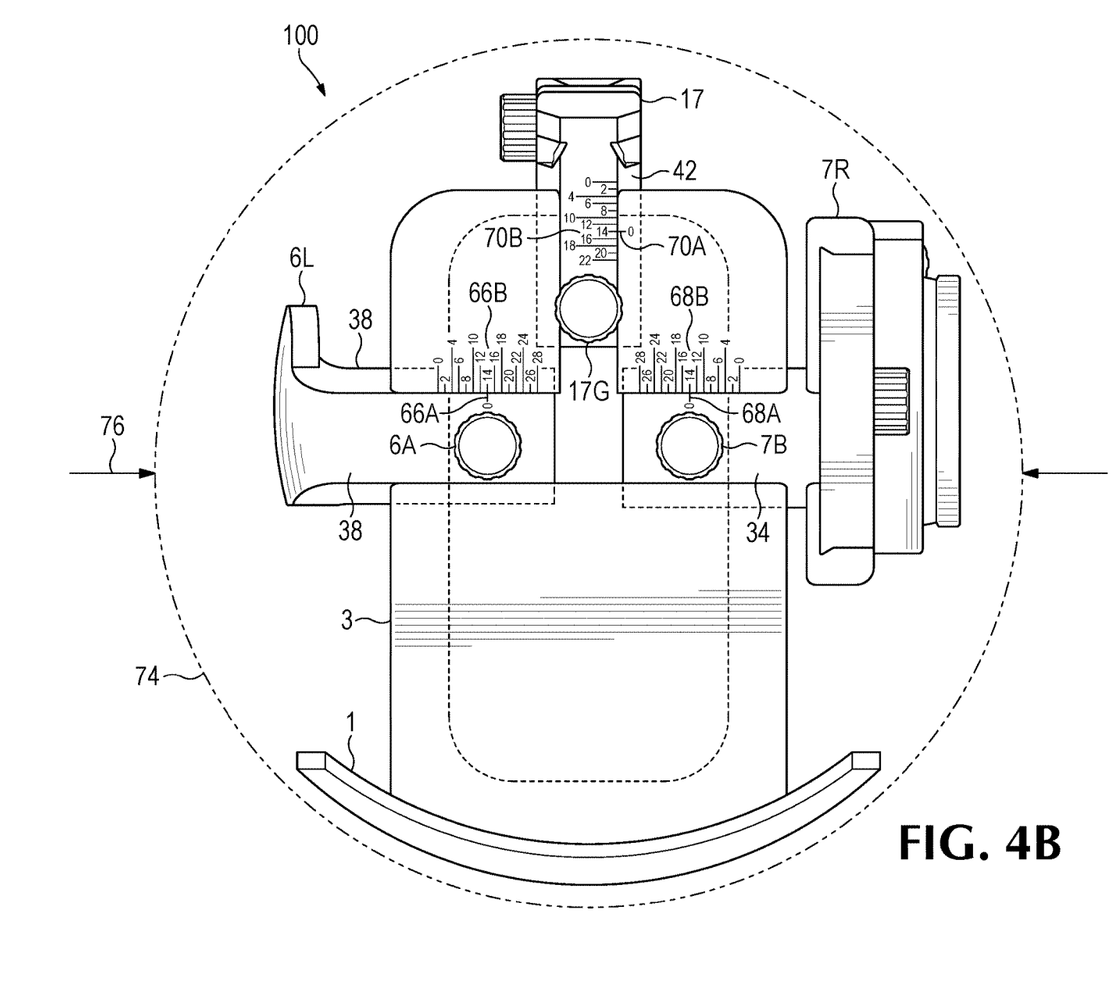

FIGS. 4A and 4B show multiple reference mark settings used when adjusting stereotactic frame 100. Referring first to FIG. 4A, a reference mark 60A is imprinted on side arm 7R to provide a reference point for horizontal longitudinal positions of transducer 13. A corresponding set of position markings 60B are imprinted on adjustment member 8 to identify the longitudinal position of adjustment member 8 relative to reference mark 60A in a forward or rearward direction. In one example, each gradation in markings 60B is 2 millimeters (mms) but of course this is just an example and any number of gradations and any gradation spacing can be used.

Reference marks 62A and 62D are printed on adjustment member 8 to provide reference points for vertical up and down positions of transducer cradle 9. Corresponding sets of position markings 62B and 62C are printed on transducer cradle 9, respectively, to identify the vertical up and down positions relative to adjustment member 8. For example, an upward position of transducer cradle 9 is identified by one of markings 62B relative to reference mark 62A and a downward position of transducer cradle 9 is identified by one of markings 62C relative to reference mark 62D.

Reference mark 64A is imprinted on nasal root arm 17 and corresponding position markings 64B are imprinted on adjustment member 16 to identify the angled horizontal longitudinal front and back position of adjustment member 16 relative to nasal root arm 17. For example, a forward position of adjustment member 16 is identified by one of a rear set of markings 64B relative to reference mark 64A and a rearward position of adjustment member 16 is identified by one of the forward set of markings 64B relative to reference mark 64A.

Referring to FIG. 4B, position settings 66B identify a horizontal lateral position of support arm 6L relative to a reference mark 66A. For example, one of markings 66B aligning with reference mark 66A indicates a relative lateral position of support arm 6L on the left side of stereotactic frame 100.

Position markings 68B identify a horizontal lateral position of side arm 7R relative to a reference mark 68A. For example, one of markings 68B aligning with reference mark 68A indicates a relative lateral position of side arm 7R on the right side of stereotactic frame 100.

Position markings 70B are imprinted on the surface of nasal root arm 17 to identify a vertical position relative to a reference mark 70A imprinted on column 3. For example, one of markings 70B aligning with reference mark 70A indicates a relative vertical position of nasal root arm 17 on the top of stereotactic frame 100.

FIGS. 4A and 4B also show stereotactic frame 100 located within MRI head coil 74. In one example, head coil 74 have a round outside shape with a radius 76. A height and width of stereotactic frame 100 are sized to fit within radius 76.

The curved shape of base 1 is also sized to have a conforming radius with the inside surface of head coil 74.

Figure 4C:
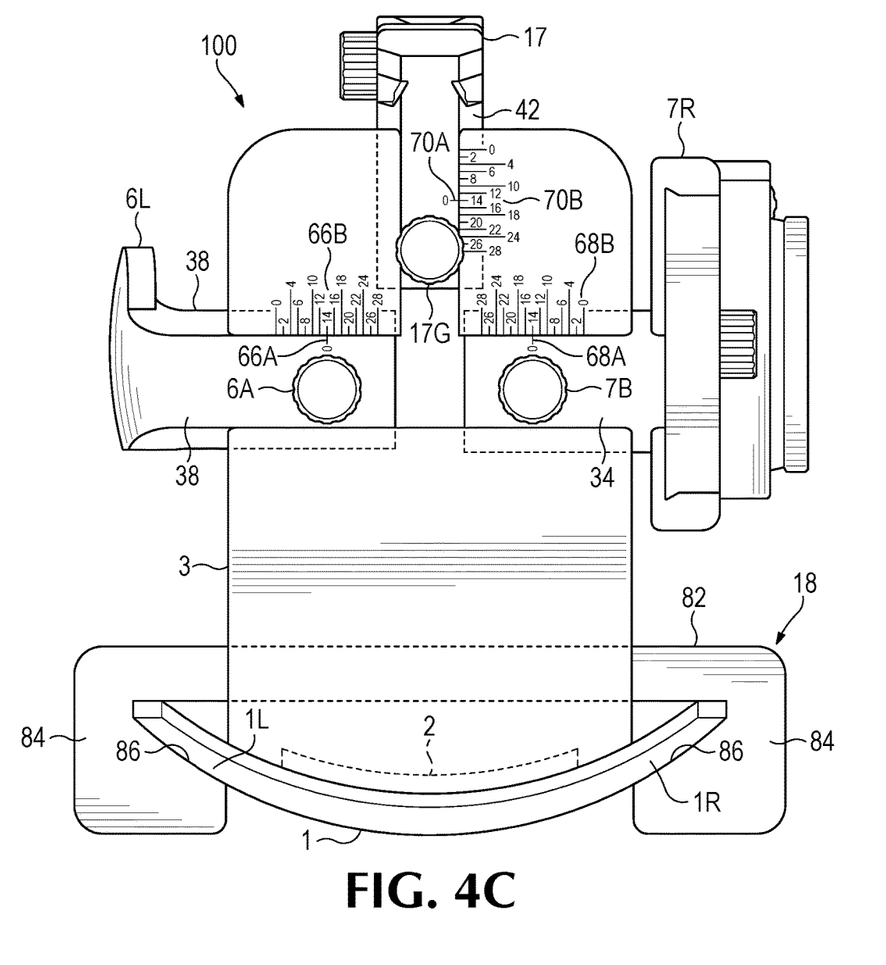
FIG. 4C shows the stereotactic frame located in a frame based support.

FIG. 4C show the alternative design of frame 100 located in a stereotactic frame support 18. In one example, base 1 of stereotactic frame 100 includes a curved cross-sectional shape to conform and sit securely on a curved convex shaped head coil. When operating off of the rounded head coil, support 18 may be attached over a back end of base 1 to provide lateral stability for stereotactic frame 100.

Support 18 may include a flat top platform 82 with legs 84 extending downward from opposite ends of platform 82. Legs 84 may include oppositely curved inside walls 86 that receive opposite lateral sides 1L and 1R of base 1. Support 18 may slide over the back end of base 1 so inside walls 86 provide support underneath lateral sides 1L and 1R preventing base 1 from rocking side to side. Support 18 may attach to stereotactic frame 100 for subsequent ultrasound treatments without a MRI machine.

Initial Alignment

Referring to FIGS. 1-4, a technician may prepare stereotactic frame 100 for attaching to head 54 of patient 53. For example, the technician may place transducer 13 into lower cradle section 10 and line up the zero marking 90B above a zero reference marking 90A. The technician then fits upper cradle section 11 on top of lower cradle section 10 and locks the two sections together with knob 13E. All other settings 60-70 described above are aligned at the zero references. The technician then attaches gel pack 14 over an inside face of transducer 13.

Patient 53 lies on their back with the back of head 54 resting on horizontal cushion 2 and the top of head 54 resting against vertical cushion 4. The technician turns knobs 6A and 7B counter-clockwise to unlock and then equally adjust left side arm 6L and tight side arm 7R until they touch opposite sides of head 54 and have the same settings 66 and 68 on each side. The technician turns knobs 6A and 7B clockwise to tighten arms 6L and 7R, respectively.

The technician may loosen knob 17G to move nasal root arm 17 vertically up or down and loosen knob 16F to move nasal root adjustment member 16 horizontally and longitudinally at angled forward or backward positions so protuberance 46 sits in the nasal root of head 54 as shown in FIG. 4A. The technician then tightens knobs 17G and 16F.

A technician may place patient 53 with attached stereotactic frame 100 into MRI device. The technician control ling an electronic power source stimulator may be in a nearby room which is safe from the magnetic field produced by an MRI device. The technician may use a functional MRI (fMRI) method that shows images from inside of the brain in head 54 and shows a target spot specific for treatment of a particular disorder.

The technician may activate transducer 13 on stereotactic frame 100 sending a Low Intensity Focused Ultrasound Pulse (LIFUP) into the brain which can be seen and recorded on an fMRI console screen as a change in a BOLD signal. The resulting location of the ultrasonic pulse is measured relative to the spot targeted for treatment. Alternatively, the ultrasonic pulse location may be verified by fMRI sequences that measure small temperature changes within the brain occurring as a result of the LIFUP stimuli.

The technician then slides patient 53 out from under the MRI device and adjusts any combination of arms 6L, 7R, and 17 and transducer assembly 80 to move the focal point of the ultrasonic pulse to the desired target location. For example, to move the focal point of the electronic pulse longitudinally back closer to the top of head 54, the technician may slide adjustment member 8 back further into side arm 7R and then tighten knob 8C.

To move the ultrasonic pulse higher vertically up toward a front face of head 54, the technician may slide transducer cradle 9 vertically upwards in adjustment member 8 and then tighten knob 9D. To pivot the focal point of the electronic pulse with respect to head 54, the technician may press on the outside of transducer 13 and then tighten knob 13E. For example, the technician may press the outside of transducer 13 at one of reference marks 90B until transducer 13 pivots against the cradle stop 57 (FIG. 2).

The MRI procedure is repeated after the focal point is reset. The MRI comparison procedure is repeated until the focal point of the ultrasonic pulse generated by transducer 13 aligns directly on the center of the target location in each different plane or axis. For example, stereotactic frame 100 may move transducer 13 in a first horizontal longitudinal x-axis with transducer adjustment member 8, a second horizontal lateral y-axis with right arm member 34, a third vertical z-axis with transducer cradle 9, and in a $4^{th}$ pivoting axis by pivoting transducer 13 inside of cradle 9.

After the focal point of the electronic pulse is aligned with the target in head 54, the technician records the stereotactic frame settings indicated by marks 60-70. The technician also records the reference mark 90B indicating which location along the circumference of transducer 13 was pressed, if any, to pivot the focal point.

Subsequent Alignments and Treatments

After applying the electronic pulse from transducer 13 on the target, stereotactic frame 100 may be removed from head 54. For example, nasal root arm 17 is removed and cushions 2, 4, and 5 and gel pack 14 removed and replaced for a next patient. The next time patient 53 is ready for therapy, the technician places head 54 back on base 1. Arms 6L, 7R, and 17 and nasal root adjustment member 16 are relocated at the previous recorded settings. Support 18 may be attached to stereotactic frame 100 for support and to prevent rocking.

Transducer assembly 80 including adjustment member 8 and transducer cradle 9 are also relocated at their previously recorded settings. For example, the technician may loosen knob 8C, move adjustment member 8 longitudinally forward or backward to the previously recorded setting, and then retighten knob 8C. The technician also may loosen knob 9D, move transducer cradle 9 vertically up or down to the recorded setting, and then retighten knob 9D. The total distance that arms 6L, 7R, and 17 move in any direction can also be varied and in one example can be readjusted in distances of 0-5 mms.

The technician also may align transducer zero setting 90B with reference zero setting 90A and then press against one of settings 90B indicated as the pivot point for pivoting transducer 13 within transducer cradle 9. The technician then may tighten knob 13E.

Transducer 13 is activated to apply another series of electronic pulses into the target in head 54. As shown in FIG. 4C, subsequent treatments may only include the electronic pulses from transducer 13 without MRI imaging. In this case, slide-on support 18 may be inserted over the back end of base 1 to prevent frame 1 from rolling.

Thus, stereotactic frame 100 holds transducer 13 so low intensity focus ultrasound pulsations can be precisely targeted into the brain while also achieving clearer images during MRI procedures. The unique design of transducer assembly 80 allows transducer 13 to be easily installed and removed. For other than substantially traverse focal point directions, cradle assembly 80 also allows transducer pivoting 52. Transducer cradle 9 also has a stop 57 to limit over pivoting of transducer 13.

The adjustable arm members provide a wide range of movement for small and large adult heads. Smaller stereotactic frames 100 may be used for smaller heads and larger frames 100 can be used for larger heads. The settings printed on frame 100 identify frame positions for multiple different planes of movement and can be recorded and reset for accurate relocation of electronic beam focal points for different patients and subsequent treatments in or out of the MRI machine. The thickness of disposable gel pack 14 can also be increased or decreased to vary the focal point of the electronic beam from transducer 13.

Stereotactic head frame 100 can be used for locating the head of a patient and adjusting the transducer 13 to its focal point is on the center of a target, recording all of the adjustable settings for accurate repeatability for subsequent treatments in any other stereotactic head frame without the need for expansive MRIs. Stereotactic frame 100 can also be used solely for holding the head still to achieve clearer imaging in an MRI. Stereotactic frame 100 can also be used for immobilizing an injured patient's head by paramedics, firemen, or other first responders prior to transporting the patient to a hospital. The stereotactic frame 100 can be used by dentists, surgeons, ophthalmologists, or any other medical personnel that may need to immobilize the head of a patient during a medical procedure. A patient may be on a gurney. A strap may be wrapped around the frame and gurney for additional immobilization and security.

In one example, stereotactic frame 100 is made from plastic, rubber, and non-metal material but can also made from other metal materials when not used in conjunction with MRI applications.

Stereotactic frame 100 may hold a variety of different transducers that can generate ultrasonic energy into the brain or other body parts at a variety of different depths to accommodate a variety of different disorders. For example, stereotactic frame 100 may be used for treating psychiatric disorders, such as depression, anxiety, Obsessive-Compulsive Disorder (OCD), bulimia, bipolar disorder, or autism. Stereotactic frame 100 also may be used to treat a variety of neurological disorders, such as epilepsy, Parkinson's, Alzheimer's, and other dementias, coma, and brain injury. Stereotactic frame 100 also may be used to treat medical conditions, such as high and low blood pressure, obesity, and endocrine and immunological disease; and perform functional diagnostics of brain circuits.

The system described above can use dedicated processor systems, micro controllers, programmable logic devices, or microprocessors that perform some or all of the operations. Some of the operations described above may be implemented in software, such as computer readable instructions contained on a storage media, or the same or other operations may be implemented in hardware.

For the sake of convenience, the operations are described as various interconnected functional blocks or distinct software modules. This is not necessary, however, and there may be cases where these functional blocks or modules are equivalently aggregated into a single logic device, program or operation with unclear boundaries. In any event, the functional blocks and software modules or features of the flexible interface can be implemented by themselves, or in combination with other operations in either hardware or software.

References above have been made in detail to preferred embodiment. Examples of the preferred embodiments were illustrated in the referenced drawings. While preferred embodiments where described, it should be understood that this is not intended to limit the invention to one preferred embodiment. To the contrary, it is intended to cover alternatives, modifications, and equivalents as may be included within the spirit and scope of the invention as defined by the appended claims.

Having described and illustrated the principles of the invention in a preferred embodiment thereof, it should be apparent that the invention may be modified in arrangement and detail without departing from such principles. Claim is made to all modifications and variation coming within the spirit and scope of the following claims.

The invention claimed is:

1. A stereotactic frame, comprising:
a base for extending underneath and holding substantially an entire head of a patient;
a column attached to and suspended vertically upwards by the base for locating next to a top of the head;
a first support arm attached to and extending from a first side of the column for locating next to a first side of the head;
a second support arm attached to a second side of the column, the second support arm suspended horizontally out from the second side of the column for locating next to a second side of the head;
an adjustment member including a first end attached to the second support arm and suspended by the second support arm in different horizontally extendable positions out from the column; and
a transducer assembly for retaining a transducer, the transducer assembly attached to a second end of the adjustment member and suspended by the adjustment member in different vertically extendable positions above the base.

2. The stereotactic frame of claim 1, wherein the transducer assembly includes an opening with rounded inside surfaces to hold the transducer at different pivoting angles.

3. The stereotactic frame of claim 1, wherein the transducer assembly includes:
a transducer cradle slidingly attached to the adjustment member to move the transducer in a vertical direction.

4. The stereotactic frame of claim 3, wherein the transducer cradle includes:
a U-shaped lower cradle section for retaining a lower portion of the transducer; and
an upper cradle section insertable into a top opening in the lower cradle section to retain an upper portion of the transducer.

5. The stereotactic frame of claim 4, further comprising a knob threadingly inserted into a side of the lower cradle member to hold the upper cradle section to the lower cradle section.

6. The stereotactic frame of claim 3, further comprising:
a first knob holding the first support arm in a horizontal lateral position on the first side of the column;
a second knob holding the second support arm in a horizontal lateral position on the second side of the column;
a third knob holding the adjustment member in a horizontal longitudinal position on the second support arm; and
a fourth knob holding the transducer cradle in a vertical position on the adjustment member.

7. The stereotactic frame of claim 1, further comprising a nasal root arm slidingly attached in a vertical direction to a top end of the column to press against a nasal root of the patient.

8. The stereotactic frame of claim 7, further comprising a nasal root adjustment member slidingly attached to the nasal root arm in a horizontal longitudinal direction.

9. The stereotactic frame of claim 1, further comprising a gel pack attached to an inside face of a transducer retained on the second support arm.

10. The stereotactic frame of claim 1, further comprising a support including:
a platform; and
side legs located on opposite sides of the platform and including oppositely inclining inside walls for receiving opposite lateral sides of a back end of the base.

11. The stereotactic frame of claim 1, further comprising cushions detachably attached to the base, column, and first support arm for pressing against the head of the patient.

12. A stereotactic frame, comprising:
a base for holding a head of a patient;
a column extending up from the base for locating next to a top of the head;
a first support arm extending from a first side of the column for locating next to a first side of the head;
a second support arm extending from a second side of the column for locating next to a second side of the head;
a transducer assembly attached to the second support arm to retain a transducer and direct ultrasonic energy from the transducer into the head of the patient, the transducer assembly including an adjustment member slidingly attached to the second support arm to move the transducer in a horizontal longitudinal direction, and a transducer cradle slidingly attached to the adjustment member to move the transducer in a vertical direction;
a first set of markings located on the column and the first support arm to identify a lateral position of the first support arm;
a second set of markings located on the column and the second support arm to identify a horizontal lateral position of the transducer;
a third set of markings on the second support arm and the adjustment member to identify a horizontal longitudinal position of the transducer; and
a fourth set of markings on the adjustment member and the transducer cradle to identify a vertical position of the transducer.

13. A stereotactic frame, comprising:
a base for holding a head of a patient;
a column extending up from the base for locating next to a top of the head;
a first laterally extending support arm extending from a first side of the column for locating next to a first side of the head; and
a second laterally extending support arm extending from a second side of the column for locating next to a second side of the head;
a nasal root arm slidingly attached in a vertical direction to a top end of the column to press against a nasal root of the patient;
a nasal root adjustment member slidingly attached to the nasal root arm in a horizontal longitudinal direction; a first set of markings located on the column and the nasal root arm to identify a vertical position of the nasal root arm; and
a second set of markings located on the nasal root arm and the nasal root adjustment member to indicate a horizontal longitudinal position of the nasal root adjustment member.

* * * * *